United States Patent [19]
Wilhelm et al.

[11] Patent Number: 5,656,673
[45] Date of Patent: Aug. 12, 1997

[54] METHOD OF REDUCING EMISSIONS FROM SOILS

[75] Inventors: John M. Wilhelm; Stephen N. Wilhelm, both of Cypress, Calif.

[73] Assignee: Niklor Chemical Co., Inc., Long Beach, Calif.

[21] Appl. No.: 563,175

[22] Filed: Nov. 27, 1995

[51] Int. Cl.$^6$ ............................ A01N 29/02; A01N 33/18
[52] U.S. Cl. ........................ 514/740; 504/116; 514/746
[58] Field of Search ..................... 504/116; 514/746, 514/740

[56] References Cited

U.S. PATENT DOCUMENTS

| | | | |
|---|---|---|---|
| 1,962,806 | 6/1934 | Clapp | 47/9 |
| 2,006,895 | 7/1935 | Hurt | 167/20 |
| 2,119,125 | 5/1938 | Anthony | 167/20 |
| 3,812,615 | 5/1974 | Jamison | 47/9 |
| 3,920,436 | 11/1975 | Janssen | 71/65 |
| 3,940,884 | 3/1976 | Mason | 47/32 |
| 4,243,563 | 1/1981 | Ferm | 260/17 R |
| 4,300,941 | 11/1981 | Nakama | 71/65 |
| 4,551,167 | 11/1985 | Young et al. | 71/64.1 |
| 4,570,378 | 2/1986 | Wendt et al. | 47/9 |
| 4,705,816 | 11/1987 | Pole et al. | 523/132 |
| 5,118,219 | 6/1992 | Walker | 405/128 |

*Primary Examiner*—Allen J. Robinson
*Attorney, Agent, or Firm*—Fulwider Patton Lee & Utecht, LLP

[57] ABSTRACT

A method of reducing emissions from fumigant-injected soils wherein a potassium thiosulfate solution is applied to the soil surface. The method has been found to be effective for chloropicrin treated soils as well as soils treated with 1,3-dichloropropene The method provides the additional benefit of adding nutrient to the soil.

6 Claims, 2 Drawing Sheets

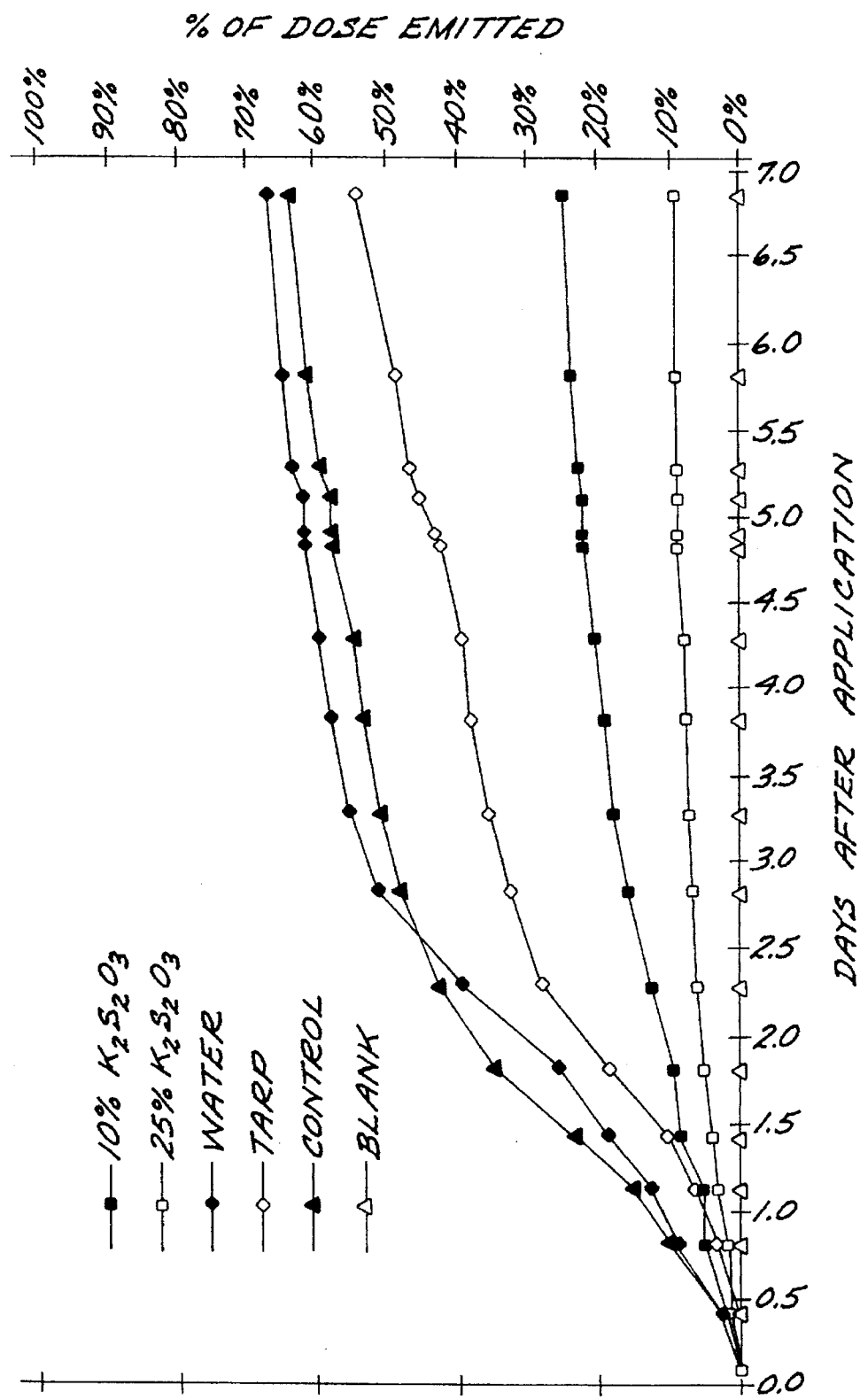

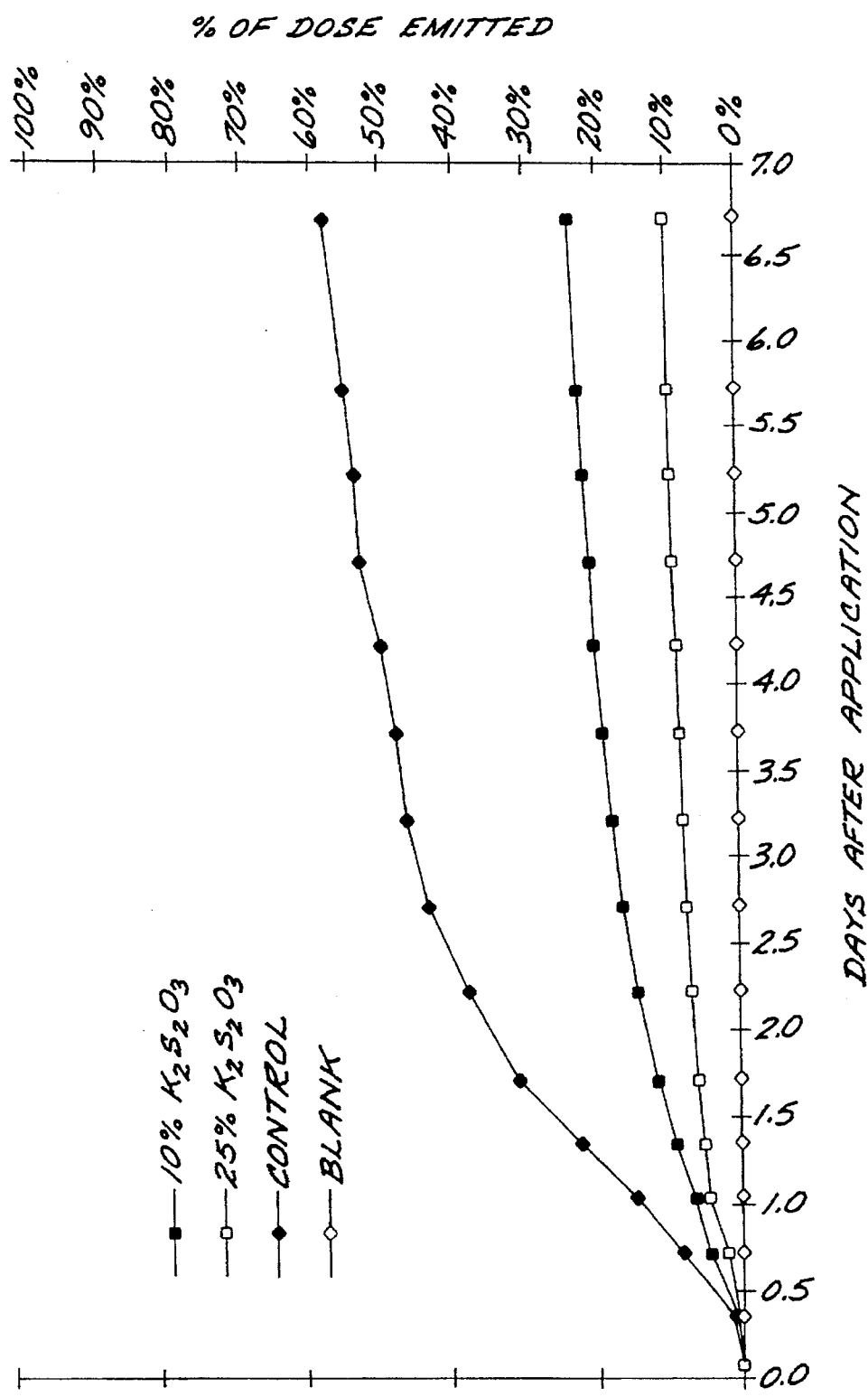

METHOD OF REDUCING EMISSIONS FROM SOILS

BACKGROUND OF THE INVENTION

The present invention generally relates to the treatment of soils for the purpose of enhancing agricultural yields. More particularly, the invention pertains to methods for preventing the escape of fumigants that are injected into the soil prior to planting. Fumigants that function as herbicides, insecticides, fungicides or nematicides are necessarily toxic in nature and it is therefore most desirable to minimize their release to the atmosphere.

Various fumigant formulations are available for the eradication or reduction of specific organism populations that are harmful to certain crops. Chloropicrin and 1,3-Dichloropropene are examples of active ingredients that are used in such formulations which may further include a variety of additives that serve to modify the chemical and physical characteristics of the composition as well as its toxicological effect.

Injection of the fumigant into the soil is typically accomplished by the use of tractor mounted chisels and/or plows. The depth of injection and the injection rate is carefully controlled so as to maximize the effect of a particular fumigant on the targeted pest or disease. Due to the volatile nature of such compositions, they tend to freely disperse through the soil as well as transfer to the atmosphere. It is therefore desirable to trap the gases in the soil in order to not only extend the time period in which the organisms are exposed but to prevent the concentrated release of the fumigant into the atmosphere. Extended residence time within the soil allows the fumigant to be absorbed, decomposed or degraded while the escape of some of the fumigant is distributed over a longer period of time.

A number of different approaches have been suggested and actually employed in an effort to trap fumigant in the soil. To date, the most widely used approach involves covering a treated field with polyethylene sheeting immediately after injection. A number of substantial disadvantages are, however, associated with such method. The material cost is significant and the deployment of acres of sheeting requires a fairly labor intensive effort. This would include the steps that must be taken to ensure that a proper seal is achieved between adjacent panels of sheeting as well as about the periphery of the covered area. The sheeting must additionally be sufficiently taut and anchored to prevent wind damage. After the treatment is complete, the sheeting must be removed and disposed of which adds substantially to the costs. Finally, it has been discovered that the polyethylene sheeting is in fact not particularly impermeable to certain fumigants which of course severely limits its efficacy.

More recently, the use of various film forming compositions have been suggested wherein a liquid composition is applied to the soil after injection of the fumigant. The material polymerizes in situ to form a film and may be formulated to decompose or degrade after a preselected period of time has elapsed or upon extended exposure to the sun's ultraviolet radiation. The material is easily tilled under prior to planting whereby it serves as a nutrient in the soil. Shortcomings inherent in these heretofore suggested systems include their limited ability to form a continuous, impermeable barrier at economically feasible rates of application.

A need continues to exist for an inexpensive, easily applied and environmentally compatible system that prevents or reduces the escape of fumigant from treated soils.

SUMMARY OF THE INVENTION

The present invention provides an effective method for preventing the escape of fumigant from soil. The method requires the application of a potassium thiosulfate solution to the surface office soil immediately after injection of the fumigant. Although no visible barrier is formed, the escape of fumigant is nonetheless substantially curtailed. The potassium thiosulfate is a rich source of potassium and sulfur nutrients readily available for uptake by the subsequently planted crop.

These and other features and advantages of the present invention will become apparent from the following detailed description of a preferred embodiment which, taken in conjunction with the accompanying drawings, illustrates by way of example the principles of the invention.

BRIEF DESCRIPTION OF THE DRAWINGS

FIG. 1 is a graph illustrating cumulative emission data of chloropicrin from soil treated in accordance with the method of the present invention; and FIG. 2 is a graph illustrating cumulative emission data of 1,3-Dichloropropene from soil treated in accordance with the method of the present invention.

DETAILED DESCRIPTION OF THE PREFERRED EMBODIMENTS

The invention comprises a method for treating fumigant injected soil in order to reduce the release of the fumigant to the atmosphere. Prior to planting, the fumigant is injected into the soil at a preselected depth and at a preselected application rate. The soil is then treated in accordance with the present invention. After a sufficient period of time has passed to enable the fumigant to perform its biocidal function, the field is properly prepared and the crop planted.

After much testing mad experimenting with various formulations, it has been found that a compound previously used in foliar applications and as an irrigation additive is extremely effective in reducing fumigant emissions. In fact, it is has been demonstrated to be substantially more effective the polyethylene sheeting and additionally serves the purpose of adding nutrients to the soil.

The method of the present invention includes the step of spraying a solution of potassium thiosulfate on the surface of the soil after injection of fumigant. While its efficacy appears to be function of concentration, a sufficiently effective and economic application rate has been found to be 460 gallons/acre of a 10% concentration.

The following experiment was conducted to assess the efficacy of the method of the present invention:

A series of test beds were prepared in the form of polyethylene vessels, 14" high×11.75" diameter, with airtight lids. Each vessel was filled to within 2" of its rim with sturdy loam soil compacted to 1.5 $g/cm^3$. In order to provide access to the soil for the purpose of injecting fumigant without disturbing the head space over the soil, a horizontal injection tube was fitted extending through the wall of each vessel and terminating at its center, 8" below the surface of the soil. A rubber septum covered the mouth of the injection tube to facilitate the injection of fumigant via a needle using a gas tight glass syringe. The head space over the soil was continually flushed with fresh air at a rate of about 80 ml/min to ensure at least one complete air change every hour. The air was dram through a first set of sorbent tubes to filter out contaminants into the head-space and subsequently withdrawn through a second set of sorbent tubes by the action of a pump. At about eight hour intervals, the second set of sampling tubes was removed and analyzed for the amount of fumigant that had been absorbed. Analysis was performed using standard gas chromatography techniques. Average cumulative emission curves were then generated.

A first series of experiments was structured so as to evaluate of the efficacy of potassium thiosulfate to reduce the emission of chloropicrin from treated soil. The surface of a first test bed (in triplicate) was sprayed with a 10% solution of $K_2S_2O_3$ (balance water) at an application rate of 460 gal/acre, a second test bed (in triplicate) was treated with a 25% solution of $K_2S_2O_3$ (balance water) at an application rate of 920 gal/acre, a third (in triplicate) was treated with water at 920 gal/acre, a fourth (in triplicate) was left untreated (control) and a fifth was not fumigated nor treated (blank). The soil surface of a sixth sample (in duplicate) was covered with a polyethylene tarp which was removable without disturbing the air-tight lid. A dose of chloropicrin ($CCl_3NO_2$) equivalent to approximately 350 lbs/acre, was injected and air samples were withdrawn for analysis 2 to 3 times per day for a total of 7 days. The tarp was withdrawn from over the tarped soil after a total of five days to simulate field practice.

FIG. 1 graphically illustrates the collected data in cumulative form. It is to be noted that under unhindered conditions, over the course of seven days, about 60-70% of the chloropicrin was emitted. Water, applied to the surface at a rate equivalent to 920 gal/acre, had no apparent effect on such emissions while the polyethylene tarp was only minimally effective in reducing the emission. The high concentration (25%), high application rate of $K_2S_2O_3$ reduced emissions to less than ⅕ of the tarped soil while the more economical application rate (10%) cut emissions by more than half.

A second series of experiments was structured so as to evaluate the efficacy of potassium thiosulfate to reduce the emission of 1,3-dichloropropene from treated soil. The surface of a first test bed (in triplicate) was sprayed with a 10% solution of $K_2S_2O_3$ (balance water) at an application rate of 460 gal/acre, a second test bed (in triplicate) was treated with a 25% solution of $K_2S_2O_3$ (balance water) at an application rate of 920 gal/acre, a third (in duplicate) was left untreated (control) and a fourth was neither treated nor fumigated (blank). A dose of 1,3-dichloropropene ($C_3H_4Cl_2$) equivalent to approximately 200 lbs/acre was injected and air samples were withdrawn for analysis 2-3 times per day for a total of 7 days.

FIG. 2 graphically illustrates the collected data in cumulative form. Emissions were again very significantly reduced by the 25% solution while the 10% solution reduced emissions by well over half.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A method for reducing emissions of chloropicrin from soil, comprising the steps of:

injecting chloropicrin into said soil; and applying a solution of potassium thiosulfate to the soil's surface.

2. The method of claim 1 wherein said solution comprises in excess of 10% potassium thiosulfate in water.

3. The method of claim 2 wherein said solution is applied at a rate of about 460 gallons/acre.

4. A method for reducing emissions of 1,3-dichloropropene from soil, comprising the steps of:

injecting 1,3-dichloropropene into said soil; and applying a solution of potassium thiosulfate to the soil's surface.

5. The method of claim 4 wherein said solution comprises in excess of 10% potassium thiosulfate in water.

6. The method of claim 4 wherein said solution is applied, at a rate of about 460 gallons/acre.

* * * * *